United States Patent [19]

Alt

[11] Patent Number: 4,846,195
[45] Date of Patent: Jul. 11, 1989

[54] IMPLANTABLE POSITION AND MOTION SENSOR

[75] Inventor: Eckhard Alt, Munich, Fed. Rep. of Germany

[73] Assignee: Intermedics, Inc., Angleton, Tex.

[21] Appl. No.: 170,251

[22] Filed: Mar. 18, 1988

[30] Foreign Application Priority Data

Mar. 19, 1987 [DE] Fed. Rep. of Germany ....... 3709073

[51] Int. Cl.4 .............................................. A61B 5/10
[52] U.S. Cl. ................................ 128/782; 128/419 PG
[58] Field of Search ............ 128/782, 419 PG, 419 D

[56] References Cited

U.S. PATENT DOCUMENTS

| | | | |
|---|---|---|---|
| 3,163,856 | 11/1961 | Kirby | 128/782 |
| 4,428,378 | 1/1984 | Anderson et al. | 128/419 PG |
| 4,722,342 | 2/1988 | Amundson | 128/419 PG |
| 4,771,780 | 9/1988 | Sholder | 128/419 PG |
| 4,782,836 | 11/1988 | Alt | 128/419 PG |

FOREIGN PATENT DOCUMENTS 7904549 12/1980 Netherlands ........................ 128/782

*Primary Examiner*—Kyle L. Howell
*Assistant Examiner*—K. Schaetzle
*Attorney, Agent, or Firm*—Russell J. Egan; John R. Merkling

[57] ABSTRACT

An implantable medical device for controlling a physiological function includes functional apparatus for controllably duplicating the selected normal physiological function of the patient's body. A sensor detects the physical orientation of the implanted medical device within the body, which is indicative of whether the patient is standing, sitting or reclining. The sensor is also responsive to forces of acceleration on the medical device within the body, indicative of the state of rest or activity movement of the patient. Apparatus in the device is responsive to the physical position and the physical state of the patient, as detected by the sensor, to control the duplication of the normal physiological function according to that position and state. In one embodiment, the medical device is a cardiac pacemaker and the physiological function is heart rate. The sensor of that embodiment includes a chamber, a mercury ball confined within the chamber, and a multiplicity of electrodes within the chamber for making or not making electrical contact with the ball to signify the physical orientation of the medical device. The electrodes are disposed about a surface of the chamber against which the ball normally resides, such that movement of the patient causes movement of the ball and interrupted makings of contact between electrodes.

14 Claims, 3 Drawing Sheets

IMPLANTABLE POSITION AND MOTION SENSOR

BACKGROUND OF THE INVENTION

The present invention relates generally to implantable medical devices, and more particularly to an implantable device for detecting the position and movement of the patient. Such devices according to the invention are useful for influencing a patient's bodily functions in conjunction, for example, with cardiac pacemakers, defibrillators, drug infusion pumps, and the like.

A survey of "therapy with rate adaptive cardiac pacemakers" is presented in the article of the same name by E. Alt. et al., published in the journal Herz/Kreislauf 18, No. 11/86, pp. 556 to 564. One section of this article, beginning on p. 560, is devoted to rate adaptive cardiac pacemakers in which the pacing rate is controlled with reference to the measurement of physical activity. An activity sensor consisting of a piezoelectric acceleration sensor located within the pacemaker is provided for detecting the jolts, accelerations and oscillations experienced by the patient in whom the pacemaker is implanted, during physical exercise. The pacing rate is then adaptively regulated in accordance with the intensity of the vibrations that occur and are transmitted throughout the body. Such a cardiac pacemaker is capable of rapid response to commencement of exercise by the pacemaker patient, but it has various disadvantages, such as the inability to maintain adequate continuing increase of pacing rate with ongoing further increase in exercise, and also in distinguishing and appropriately responding to different physical activities having essentially the same intensity of stress.

A further problem in adapting the pacing rate in a physiologically appropriate manner for the patient involves the adequacy of the cardiac pacemaker's rate response when the patient is at rest or undergoes a change in his rest behavior. For example, the fact that a patient's metabolism slows down during sleep is essentially disregarded in the operation of known activity-controlled cardiac pacemakers, because such pacemakers typically have been designed merely to provide a step heart rate increase in response to stress without regard to the nature and extent of the stress. On the other hand, cardiac pacemakers which utilize known representative metabolic parameters to control the pacing rate, that is, parameters such as breathing rate, blood oxygen saturation and the like, have the disadvantage of requiring that the applicable parameter be measured by separate sensors which are outside the confines of the cardiac pacemaker. Also, the latter pacemakers tend to react more slowly to the patient's need for an increase of heart rate with onset of exercise, than do the activity-controlled pacemakers.

Furthermore, such pacemakers are incapable of duplicating the orthostasis reaction of a healthy person in the patient in which the pacemaker is implanted. This type of reaction occurs in a healthy person upon standing from a position of rest, whether lying or sitting, whereupon the individual experiences a rapid compensatory increase in heart rate. When the individual is in a lying position, the venous blood readily returns to the heart from the lower extremities. However, when the person stands, the blood flow from the extremities is slowed because of gravity. This leads to a reduction in the stroke volume of the heart. In a healthy person the reaction is compensated by a reflex increase in the heart rate, but that is not the case with most cardiac patients, and there is no corresponding compensatory effect with known cardiac pacemakers.

In any event, some patients experience a dramatic drop in blood pressure when they change positions, which cannot be overcome merely by use of an implanted cardiac pacemaker. In such instances, it is customary to administer medications to the patient to support the proper blood circulation. It is desirable to limit the administration of such medicinal preparations as much as practicable, and for this and other reasons, portable or implantable drug infusion pumps have been developed that dispense medications slowly in measured concentrations and doses.

As previously noted, a patient's physical position has a considerable influence on the stroke volume of the heart. Accordingly, it may be difficult to determine and regulate the pacing rate merely by reference to measurement of the stroke volume. Therefore, a reliable interpretation of the measured values of the stroke volume would also be desirable.

It is an important object of the present invention to provide new and improved means for controlling and regulating the heart rate of a cardiac pacemaker patient according to the position or physical attitude of the patient relative to an axis determined by gravitational pull.

Another object of the invention is to provide a control mechanism for a cardiac pacemaker by which the pacing rate, and thus the patient's heart rate, may be adjusted according to the specific physical position of the patient while in a state of rest, whereby the heart rate is regulated in a physiologically appropriate manner according to the nature of the rest position and relative changes of the rest position.

A further object of the present invention is to provide a control mechanism for a cardiac pacemaker which is also responsive to acceleration of the patient, so that, for example, when the patient arises from a supine position, the pacing rate may be increased in the same manner as would the heart rate of a healthy person with a normal heart.

SUMMARY OF THE INVENTION

Briefly stated, the present invention is based on the proposition that an implantable medical device which is capable of detecting both the degree of movement of the patient and the position (i.e., the arrangement of bodily parts) of the patient may be utilized not only to monitor those characteristics and, as well, to develop control criteria for influencing physiological functions in the presence of the full range of physical activity or inactivity of the patient. A basic premise of the invention is to utilize the influence of gravity on a movable mass in order to perform position and/or motion sensing in an implantable device, whereby to determine the position of the patient, to ascertain whether he is in a condition of rest or exercise, and, with certain other features of the detection system for the movable mass, to assess the intensity or vigorousness of the exercise.

In its broader aspects, a preferred embodiment of the invention resides in an implantable medical device for controlling a physiological function of the body of the patient in whom the device is implanted which includes functional apparatus for controllably duplicating the selected normal (physiological) function of the body, a sensor for detecting the physical position of the implanted medical device within the body, and thereby, whether the patient is standing or reclining, the sensor having means for detecting acceleration of the medical device within the body, and thereby, whether the patient is at rest or undergoing movement, and control apparatus coupled to the functional apparatus and responsive to the physical position and state of rest or exercise of the patient as detected by the sensor, for controlling the duplication of the normal physiological function by the functional apparatus according to that physical position and the state of rest or exercise.

In the presently preferred embodiment, the medical device is a cardiac pacemaker and the physiological function to be duplicated is the normal heart rate as it adapts to the position and conditions of rest and exercise of the patient. The sensor comprises a chamber, a mercury ball confined within the chamber, and at least two electrodes within the chamber for making or not making electrical contact with the ball to signify the physical attitude or orientation of the medical device relating to the direction of gravitational pull. To more clearly detect the nature and extent of the patient's movements, a multiplicity of electrodes is disposed about a surface of the chamber against which the mercury ball normally resides, whereby movement of the patient causes movement of the ball and numerous interrupted makings of contact between adjacent ones of the multiplicity of electrodes.

Devices implemented according to the invention are useful not only for controlling associated implanted (or external) medical devices which regulate one or more bodily functions, such as a pacemaker, defibrillator, drug infusion pump, and so forth, but for independently determining the position of the patient's body and whether the patient is resting or moving about. Moreover, if the patient is moving, the inventive device has the capability to detect the intensity of the body's movement; that is to say, whether the individual is undergoing mild, moderate or vigorous exercise. This capability to detect the patient's physical attitude or posture, and, as well his state of movement, if any, is important in and of itself in situations such as where the patient must be monitored continuously.

Therefore, it is a broader object of the present invention to provide an implantable mechanism which may be utilized to sense both the physical position and the state of rest or movement of the patient, and, if the patient is moving, the degree of the movement, for control purposes.

The output signals of the sensor mechanism can serve either to control the selected physiological functions of the patient directly or to evaluate such a control with the aid of another parameter. For example, if the inventive device is used as part of a cardiac pacemaker, it can determine readily whether the patient is at rest—indeed, the state of his posture, e.g., whether he is lying or sitting—or is moving and the nature of that movement. The output signals of the sensor may therefore be evaluated to generate a control signal for the pacemaker pulse generator, by which to provide an adequate pacing rate response. Other advantages and improvements are also possible in conjunction with the sensing device of the invention. By way of further example, the pacemaker utilizing this technique may employ yet another physiological parameter, e.g., one dependent on the metabolism, with the two parameters being used for mutual control of the stimulation rate of the pacemaker.

SUMMARY OF THE DRAWINGS

The above and other objects, features and attendant advantages of the invention will become more readily apparent from a consideration of the following detailed description of a presently preferred embodiment thereof, when taken in conjunction with the accompanying figures of drawing, in which.

DETAILED DESCRIPTION OF THE PREFERRED EMBODIMENT

Figure 1:
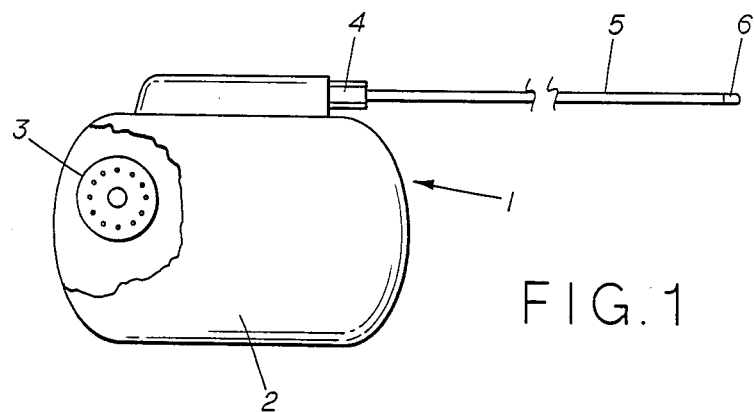
FIG. 1 is a plan view, partly in section, of an implantable cardiac pacemaker having integral therewith a position and motion sensor according to the presently preferred embodiment of the invention.

Referring now to FIG. 1, an implantable cardiac pacemaker 1 which is of conventional design (except as will otherwise be described below), in conjunction with the position and motion sensor, has a biocompatible case 2 in which substantially the entire electronic system of the pacemaker (described below with reference to FIG. 4) is contained. Also mounted within the case 2 is the presently preferred embodiment of position and motion sensor 3. A conventional pacemaker catheter lead 5 having a stimulating cathodic electrode 6 at its tip is adapted for intravenous insertion to place the electrode(s) in proper position in one or both chambers at the right side of the patient's heart (depending on whether the pacemaker is a single or dual chamber device). The lead 5, which may also have an anodic reference electrode adjacent the tip for bipolar stimulation of the heart, includes a male connector at its proximal end to mate with a female connector in a coupling mechanism 4 integral with the pacemaker case 2.

Figure 2:
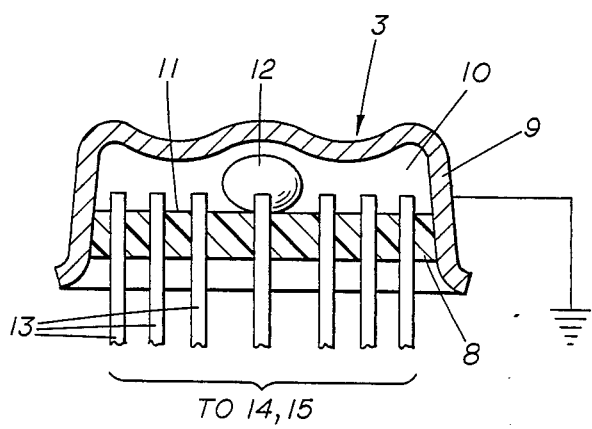
FIG. 2 is a cross-sectional side view of the position and motion sensor embodiment utilized in the environment of the pacemaker of FIG. 1.
Figure 3:
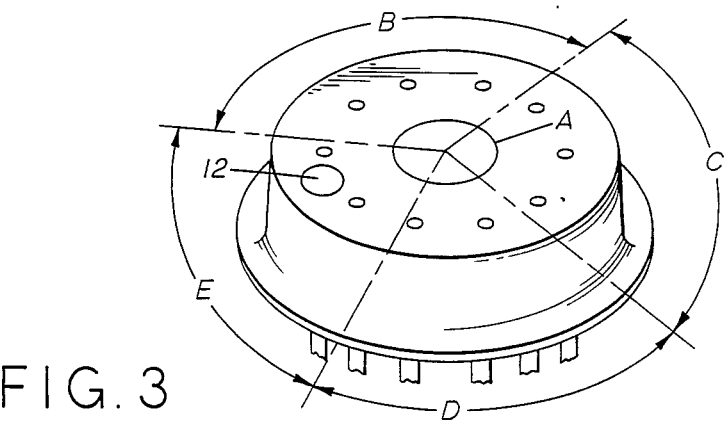
FIG. 3 is a perspective view of the position and motion sensor embodiment of FIGS. 1 and 2, partly in phantom or transparency to more clearly depict the relationship of its component parts.

The preferred embodiment of position and motion sensor 3 is shown more clearly in FIGS. 2 and 3. The sensor has a housing 7 which includes a circular disk-like wall 8 of electrically insulative material such as glass, and a lid portion 9 of electrically conductive material to which insulative wall 8 is fastened to form a hermetic seal therewith. Within the chamber 10 of this configuration, a mercury ball 12 is confined to reside against and move about on the interior surfaces, such as 11, formed by wall 8 and lid 9. A plurality of electrically conductive pins 13 project into the chamber 10 through the wall 8, the pins being fastened to the wall to form an hermetic seal therewith.

In the preferred embodiment of sensor 3 shown in FIG. 1, twelve evenly spaced pins project in a circular array of slightly smaller diameter than the diameter of wall 8 at surface 11. It will be understood that a greater or smaller number of pins may be used, depending in part on their spacing relative to the cylindrical side surface of lid 9 and the size of mercury ball 12. Each of pins 13 is an electrical contact or electrode at the point of entry into chamber 10, each being connected via circuitry in the pacemaker to the appropriate pole of a battery or other suitable portable power supply, the other pole of which constitutes or is connected to a point of reference potential. The battery, of course, is physically housed within the case 2 of the pacemaker. The electrically conductive lid 9 of the sensor is connected to the point of reference potential (electrical ground).

The surface 11 of the chamber formed by insulative wall 8 is smooth and constitutes a running surface for the mercury ball 12. When the physical orientation of the sensor 3 is such that surface 11 is substantially perpendicular to the direction of gravitational pull, i.e., the patient is in a horizontal position, the ball will move to the center of that surface (or to the center of lid 9). When the running surface 11 is substantially parallel to the direction of gravitational pull but the sensor 3 is undergoing acceleration, the mercury ball 12 will move along that surface in contact with the electrically conductive lid 9 and as well, because of the size of the mercury ball, in and out of contact with one or more of the electrodes 13. To that end, when lid 9 and wall 8 are assembled to form chamber 10, the electrodes 13 are disposed close to the periphery of the wall 8 and yet sufficiently spaced from the intersection of the wall with the lid such that the size of the mercury ball permits it to contact at least one electrode and the surface of the lid near that point of intersection to create a closure of the electrical contacts, that is, of the lid with the respective electrode pin. Furthermore, the formation of the chamber is such that the mercury ball will not touch any contact pin or the electrically conductive lid in the central area A (as shown in FIG. 3), when the interior surface of the chamber formed by wall 8 is substantially perfectly horizontal relative to the direction of gravitational pull. Thus, with the orientation of sensor 3 as shown in FIG. 1 within the pacemaker housing, and the usual orientation of the pacemaker after implantation in the patient's body, the sensor is oriented vertically when the patient is standing in an upright position and is oriented horizontally when the patient is in a prostrate position (either prone or supine). In the perfectly horizontal position, the mercury ball will be disposed in the central area of the interior surface of the chamber formed by wall 8 and thus will reside in a depression (not shown) at that location in the surface, such that it is not in contact with any of the electrodes 13.

However, when the patient moves sufficiently from the prostrate position, the mercury ball will move rapidly toward the outer periphery of surface 11, and thereby establish contact with at least one of the electrodes 13 and with the electrically conductive lid 9. Thus, an electrical connection is established between the point of reference potential to which lid 9 is connected and a different point of electrical potential within the circuit of the pacemaker. This will cause current to flow and thereby generate an electrical signal which may be used to determine the position of the patient or, as will be explained in greater detail below, the acceleration of the sensor and thus of the patient, as a result of forces acting on the mercury ball.

It will be observed that the lid is formed with a depression such that in the normal orientation of the pacemaker in the patient's body, when the patient is in a prone position, the mercury ball will reside within the depression in the lid and will not contact any of the electrodes 13 exposed at the interior surface 11.

As shown in FIG. 3, the contact pins 13 may be evenly spaced from one another close to the periphery of surface 11. Whether they are uniform in spacing or are unevenly spaced, they may be assigned to a map or plot by which individual sectors are laid out relative to surface 11 such that the electrical connections created by the location of the mercury ball will readily indicate the sector in which the ball is located and, thus, the relative physical position of the patient. In the embodiment of the invention shown in FIG. 3, four sectors, B, C, D and E have been designated for the sensor. It will be understood that the number of sectors and the number of contact pins or electrodes 13 encompassed by each sector may be varied according to the extent to which it is desired to discern specific positions and extent of acceleration or movement of the device. In the context of the presently preferred embodiment, the desire is to provide a greater degree of control of the rate response of the cardiac pacemaker in which the sensor 3 is housed (or with which the sensor is associated) such that the stimulation rate developed by the pacemaker tends to duplicate the normal heart rate that would be experienced by a healthy person under the same conditions of the resting position of the body or of exercise.

Figure 4:
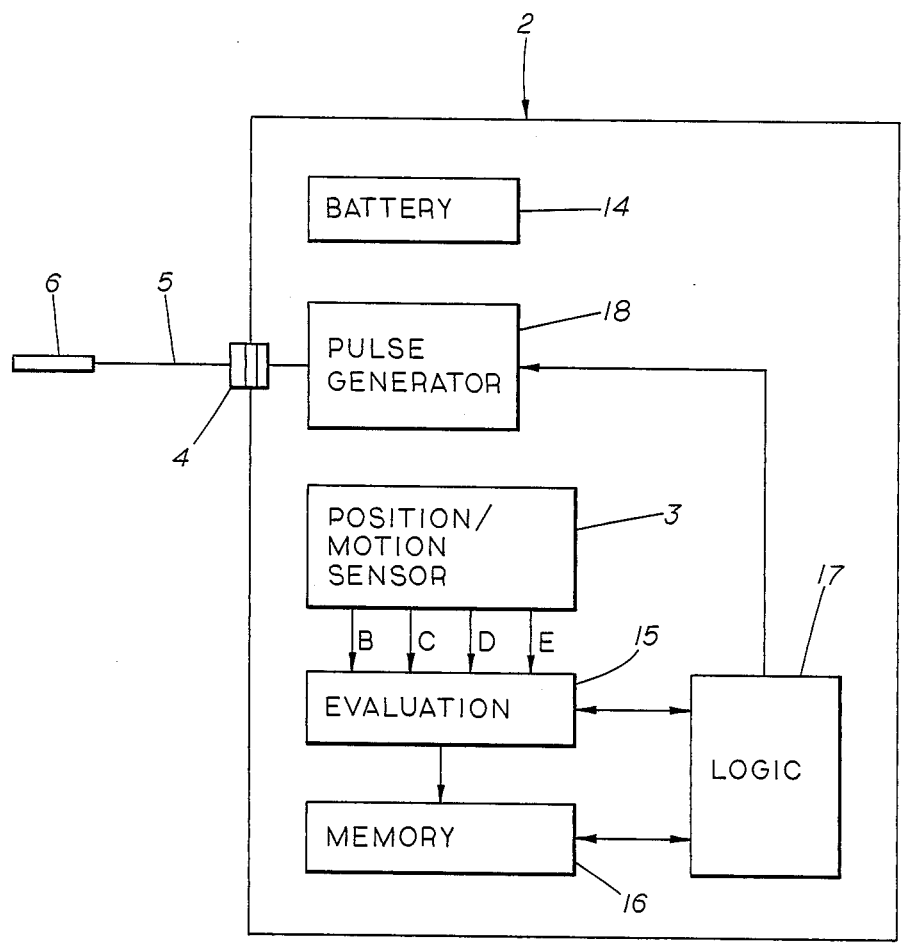
FIG. 4 is a schematic block diagram of the cardiac pacemaker and integral position and motion sensor embodiment of FIG. 1.

Referring now to FIG. 4, the case 2 of the pacemaker (more properly, the "pulse generator" portion of the pacemaker) houses the battery or set of battery cells 14, the pulse generator and associated circuitry, and the position/motion sensor 3 from which signals representative of the location of the ball within sectors B, C, D and E are derived. The circuitry housed within the pulse generator case 2 includes an evaluation circuit 15, memory 16, logic circuit 17, and pulse generator 18.

As the mercury ball makes contact between various ones of the electrodes 13 and the conductive lid 9, signals representative of the location of the ball in the respective sectors are generated and inputted to the evaluation circuit 15. From a predetermined mapping of the relative position or orientation of the sensor 3 within the patient's body, the indication of the sector within which the ball is located provides definitive information of the physical position of the patient himself. For example, referring once again to FIGS. 1, 3 and 4, it will be observed that when the patient is standing upright, the sensor 3 is in a vertical position in which the mercury ball has moved to and is lying in sector E where it is in electrical contact with an electrode in that sector as well as with the lid 9.

The signals shown in FIG. 4 as deriving from electrodes in the various sectors within sensor 3 are developed from the electrical contacting of the ball with lid 9 and particular electrodes(s) 13, from which the precise location of the ball within a particular sector is readily determined. If the ball were of sufficient size to contact two electrodes at the same while being in contact with lid 9, that, too, would be a precise indication of the location of the ball within chamber 10.

The patient is either standing upright or sitting upright when mercury ball 12 is in sector E (FIG. 3), assuming that sector E lies in the bottom portion of sensor 3 as viewed in FIG. 1. This information is supplied from evaluation circuit 15 to memory 16 and to logic circuit 17. The logic circuit provides a control function according to an algorithm stored in memory, in response to the specific location of the mercury ball, as determined by the evaluation circuit. The logic circuit then supplies control signals to pulse generator 18 to regulate the frequency of the pulses generated by the pulse generator and thereby adaptively control the stimulation of the patient's heart, and thus, the patient's heart rate. For example, if the patient has been standing for a period of time without any significant movement, the pacing rate and, thus, the patient's heart rate, is controlled to be at a stable rate by the pulse generator. However, if the patient arises from a reclining position to an upright position (whether sitting or standing), the control exercised on the pulse generator is to increase the pacing rate, corresponding to the orthostasis phenomenon experienced by a healthy person with a normal functioning heart under the same conditions.

It will be understood that motion sensor 3 is mounted within the pulse generator case 2, and that the case is implanted into the body of the patient with such orientation that the output signals of the motion sensor can be evaluated in a position-dependent fashion, on the one hand, and according to the number and frequency of the openings and closings indicative of forces of acceleration on the mercury ball, on the other hand. The amplitudes of movements of mercury ball 12 are evaluated from sector or individual electrode locations at which the openings and closings occur. Thus, by way of further example, if the mercury ball 12 were residing in sector E in the location shown in FIG. 3, and the movements of the ball caused closings in sector C followed again by closings in sector E, it would be apparent that the mercury ball had traversed the entire diameter of the inner chamber 10.

Figure 5:
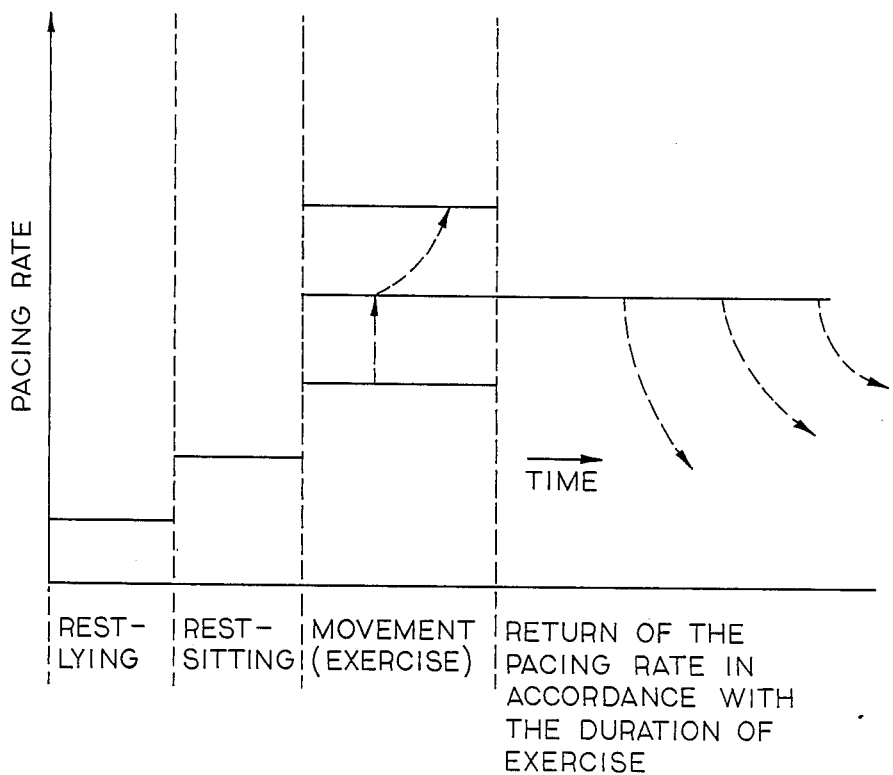
FIG. 5 is a plot or chart diagram useful to explain the manner in which control of the pacing rate of the cardiac pacemaker is maintained using a position and motion sensor according to the invention.

As previously described, when the patient is prostrate, either in the prone or a supine position, mercury ball 12 will be located in the area designated A of chamber 10; hence, no contact is made by the mercury ball with any of the electrodes 13 and no output signal appears at any of the contact pins. In those circumstances, the stimulation rate of pulse generator 18 is adjusted by the logic circuit 17 in conjunction with the outputs or evaluation circuit 15 and memory 16 to an appropriately low value indicative of the patient being at "rest/lying", as shown in FIG. 5. The designation of individual sectors shown in FIG. 3 also facilitates the capability of the sensor to ascertain other physical orientations of the patient. For example, the patient may be determined to be lying at rest on his side—either side—in which event the stimulation rate and thus the patient's heart rate will be held by the pulse generator at the same relatively low value according to the "rest/lying" condition in FIG. 5. It will be observed then that the "rest/lying" condition for the heart rate may be maintained without regard to whether an electrical contact is established between a contact pin (electrode) 13 and lid 9, at least if there is no repeated opening and closing of connections between the contact pin and the lid through the ball or if only a predetermined small number of interrupted openings and closings take place. In the event that the sensor 3 is somehow reoriented within the patient's body as a result of movement of the pacemaker pulse generator within the implantation pocket, the mapping or plotting of the sectors of FIG. 3 may be modified according to this change in orientation, by non-invasive programming of memory 16 in conjunction with the output signals from the position/motion sensor 3, in any conventional manner. When the pacemaker patient arises from the prone or supine position to a position of "rest/sitting", or "rest/standing", the mercury ball 12 will move into one of the lower sectors E or D as a result of gravity. The pacemaker is readily programmed such that an output signal from either of the sectors D and E to evaluation circuit 15 will result in an increase in the pacing rate, for example by 15 beats per minute, as shown in FIG. 5.

If the patient then commences activity such as walking, climbing stairs or running, the mercury ball 12 will move back and forth in chamber 10 at varying speeds which depend upon the intensity of the movements. As a consequence, there will be interrupted makings of contact between the mercury ball, the respective electrodes 13 and the surface of conductive lid 9, at various frequencies as this oscillating movement of the ball continues. The number of openings and closings and the affected electrodes 13 will be indicative of the intensity and direction of the movements and is readily determined by the evaluation circuit 15 according to the specific preprogrammed settings of memory 6 with logic circuit 17. The evaluation circuit also supplies inputs to the memory for storage therein according to the duration and extent of the exercise and the period of exercise.

Thus, by virtue of the predetermined mapping of chamber 10 into individual sectors and the evaluation of output signals of the motion sensor as to the number and frequency of openings and closings and also the amplitude of the oscillating movement of the mercury ball 12, the pacemaker circuitry is able to determine precisely the specific state of the patient. In particular, it may readily be determined whether a patient is simply undergoing a low level of physical activity such as walking at a slow pace or greater activity such as jogging, to adaptively regulate the pacing rate of the pulse generator by the logic circuitry 17. As shown in FIG. 5, two positions of rest, namely "rest/lying" and "rest/sitting" (or "rest/standing") dictate two separate but relatively low heart rates corresponding to the normal heart function for these positions. Three stimulation rate responses are indicated for different states of exercise, with progressively higher rates. Transition to a higher rate response may be timed or controlled by signals derived from the motion sensor through the openings and closings created by the movement of the mercury ball 12. It will be understood, of course, that these increases in frequency may be programmed by means of predetermined settings within memory 16 such that the increases are continuous, rather than stepped responses.

The speed of return of the rate from an elevated rate to the resting rate after completion of the exercise interval will depend in large part upon the duration of that exercise period, and is controlled by the logic circuit 17 through the preprogrammed information within memory 16. Preferably, the return to the resting rate following exercise is controlled to occur more slowly with increasing duration and intensity of the exercise. In FIG. 5, this is shown schematically by the flattening of the dotted lines indicative of the initial rapid decrease of pacing rate after the exercise session has ended and then more slowly toward the resting rate.

While a presently preferred embodiment of the invention has been described, it will be recognized by those skilled in the art to which the invention pertains that variations and modifications of the preferred embodiment may be implemented without departing from the true spirit and scope of the invention. Accordingly, it is intended that the invention be limited only to the extent necessitated by the appended claims and by the applicable rules of law.

I claim:

1. An implantable medical device for regulating a bodily function, comprising:
   means responsive to gravity and acceleration for detecting both position and motion of the patient in whom the medical device is implanted, and
   means responsive to said means for detecting controlling the regulation of said bodily function by the medical device.

2. The device of claim 1 wherein the detecting means comprises means responsive to the physical attitude of the patient for producing an electrical signal representative thereof.

3. The device of claim 2 wherein the producing means comprises a plurality of electrical sensors and a movable electrically conductive material for moving into and out of contact with at least one of said plurality of electrical sensors.

4. The device of claim 1 wherein the detecting means comprises means for electrically sensing the physical attitude of the device relative to the direction of gravitational pull and the acceleration of the device from forces other than merely gravitational pull.

5. An implantable medical device for controlling a physiological function of the body of the patient in whom the device is implanted, the device comprising
   functional means for controllably duplicating a selected normal physiological function of the body,
   sensor means for detecting the physical position of the implanted medical device within the patient's body, and thereby, whether the patient is standing or reclining,
   said sensor means including acceleration means for detecting acceleration of the body, and thereby, whether the patient is in a physical state of rest or in a physical state of movement, and
   control means coupled to said functional means and responsive to the physical position and physical state of the patient as detected by said sensor means, for controlling the duplication of said normal physiological function by said functional means according to that position and state.

6. The invention according to claim 5, wherein said medical device is a cardiac pacemaker and said physiological function is the heart rate.

7. The invention according to claim 6, wherein said sensor means comprises a chamber, a mercury ball confined within said chamber, and at least two electrodes within said chamber comprising means for making or not making electrical contact with said ball to signify the physical position of said medical device.

8. The invention according to claim 7, wherein said acceleration means comprises a multiplicity of electrodes disposed about a surface of said chamber against which said ball normally resides, whereby movement of the patient causes movement of the ball and numerous interrupted makings of contact between adjacent ones of said multiplicity of electrodes.

9. An implantable detector for use in medical applications, comprising:
   gravity sensing means for detecting both the physical attitude and the acceleration of the detector,
   means responsive to the detected attitude and acceleration for producing a signal indicative thereof, and
   means responsive to the signal for controlling a physiological function.

10. In combination with a medical device for regulating a selected bodily function, an implantable controller for said medical device, the controller comprising means adapted to be implanted in a patient's body for sensing both the body's attitude relative to a predetermined axis and the body's movement along and about said axis, and means responsive to the sensed attitude and movement for controlling the regulation of the selected bodily function by the medical device.

11. In combination with a cardiac pacemaker for regulating heart rate, an implantable controller for said pacemaker, the controller comprising means adapted to be implanted in a patient's body for sensing both the body's orientation relative to the direction of gravitational pull and the body's movement in that and other directions, and means responsive to the sensed orientation and movement for controlling the regulation of heart rate by the pacemaker whereby the heart rate is adapted to the physical position and state of rest or exercise of the patient.

12. The combination according to claim 11, wherein the controller is mounted within the cardiac pacemaker.

13. The combination according to claim 12, wherein said sensing means comprises a chamber, and at least two electrodes within said chamber providing means for making or not making electrical contact with said ball to signify the physical position of said pacemaker.

14. The combination according to claim 13, wherein a multiplicity of electrodes is disposed about a surface of said chamber against which said ball normally resides, whereby movement of the patient causes movement of the ball and numerous interrupted makings of contact between adjacent ones of said multiplicity of electrodes.

* * * * *